(12) United States Patent
Faizan et al.

(10) Patent No.: US 12,207,721 B2
(45) Date of Patent: Jan. 28, 2025

(54) PERFUME DISPERSING DEVICE

(71) Applicant: Mirza Faizan, Irving, TX (US)

(72) Inventors: Mirza Faizan, Irving, TX (US); Kimaya Rafiq Meherali, Dallas, TX (US)

( * ) Notice: Subject to any disclaimer, the term of this patent is extended or adjusted under 35 U.S.C. 154(b) by 225 days.

(21) Appl. No.: 17/976,894

(22) Filed: Oct. 31, 2022

(65) Prior Publication Data

US 2024/0138541 A1 May 2, 2024

(51) Int. Cl.
*A45D 34/02* (2006.01)
*A61L 9/14* (2006.01)

(52) U.S. Cl.
CPC ............... *A45D 34/02* (2013.01); *A61L 9/14* (2013.01); *A45D 2200/057* (2013.01); *A61L 2209/134* (2013.01)

(58) Field of Classification Search
CPC ..... A45D 34/02; A45D 2200/057; A61L 9/14; A61L 2209/134; A61L 2209/11; A61L 2209/111; A61L 2209/132; A61L 2209/133; A61L 9/125
See application file for complete search history.

(56) References Cited

U.S. PATENT DOCUMENTS

| | | | | |
|---|---|---|---|---|
| 2005/0212151 A1* | 9/2005 | Malle | ...................... | A61L 9/122 261/30 |
| 2005/0279865 A1* | 12/2005 | Thomason | ................ | B05B 7/16 239/525 |
| 2022/0339650 A1* | 10/2022 | Mohorovic | ......... | B05B 12/1409 |
| 2023/0321683 A1* | 10/2023 | Mayet | ....................... | A61L 9/14 |

FOREIGN PATENT DOCUMENTS

FR 3057168 A1 * 4/2018 ............. A61L 9/122

* cited by examiner

*Primary Examiner* — Donnell A Long

(57) ABSTRACT

Embodiments of the present disclosure provide a perfume dispersing device for dispersing a plurality of flavours of perfume. The perfume dispersing device comprises an input unit for receiving an input from a user indicating a selection of a flavour from a plurality of flavours of perfume. The perfume dispersing device further comprises a compressor for generating pressure in an air tank of the perfume dispersing device. The perfume dispersing device comprises a processor for selecting a perfume holder from a plurality of perfume holders included in the perfume dispersing device based on the input from the user. Each perfume holder of the plurality of perfume holders contains a specific flavour of the plurality of flavours of perfume. The air tank releases air pressure to the selected perfume holder. The perfume holder disperses the flavour indicated by the input from the user.

14 Claims, 4 Drawing Sheets

PERFUME DISPERSING DEVICE

TECHNICAL FIELD

The present disclosure relates generally to a perfume dispersing device. More particularly, it relates to dispersing a selected flavour of perfume.

BACKGROUND

People use perfumes for various purpose, such as relaxation, psychological stability, and ventilation. Scents are good smells from flowers, fragrances, and perfumes. It is a long-known effect that certain scents can affect a person's psychology and emotions.

For buying a perfume, user generally have to go to physical shop for selecting preferred flavour of the perfume. Perfumes are generally provided in liquid form and can be stored and used in any container having a device capable of ejecting the liquid. In general, a user has a container containing perfume in a predetermined place, or uses perfume by spraying perfume on a part of the body such as a wrist or neck, or spraying on clothes.

Now a days, people prefer to buy everything online. However, in case of buying perfumes, the user is not able to experience the flavour of the perfume before buying it. Some of the approaches have been adopted by the manufacturer to make the user buy the perfumes. In an approach, the manufacturer send samples of available flavours to the user and then user selects the flavours from the samples. However, this process have several limitations such as costly process, time consuming process, and limited availability of samples.

Thus, there is a need for a simple and cost effective process of providing samples of different flavours of the perfume that addresses the aforesaid problems.

SUMMARY

Consequently, there is a need for an improved method and arrangement for implementing a method and system that alleviates at least some of the above-cited problems.

It is therefore an object of the present disclosure to a perfume dispersing device for dispersing a plurality of flavours of perfume to mitigate, alleviate, or eliminate all or at least some of the above-discussed drawbacks of presently known solutions.

This and other objects are achieved using a device and a method as defined in the appended claims. The term exemplary is in the present context to be understood as serving as an instance, example or illustration.

According to the first aspect of the present disclosure, a method for dispersing a plurality of flavours of perfume is disclosed. The method is performed by a perfume dispersing device. The method comprises receiving, from a user, an input indicating a selection of a flavour from a plurality of flavours of perfume. The method further comprises generating, from a compressor of the perfume dispersing device, pressure in an air tank of the perfume dispersing device. The air tank is filled with air.

The method further comprise selecting, by a processor of the perfume dispersing device, a perfume holder from a plurality of perfume holders included in the perfume dispersing device based on the input from the user. Each perfume holder of the plurality of perfume holders contains a specific flavour of the plurality of flavours of perfume. The method further comprises releasing, by the air tank, air pressure to the selected perfume holder. Furthermore, the method comprises dispersing, by the selected perfume holder, the flavour indicated by the input from the user.

In some embodiments, the perfume dispersing device is connected to a mobile device through an audio jack.

In some embodiments, the compressor draws a current from the mobile device.

In some embodiments, the air pressure is released to the selected perfume holder through a network of pipes.

In some embodiments, each pipe of the network of pipes is connected to a corresponding perfume holder of the plurality of perfume holders.

In some embodiments, the user provides the input to the perfume dispersing device via a user interface displayed on a screen of the mobile device.

In some embodiments, the flavour indicated by the input from the user is dispersed in a form of mist.

According to a second aspect of the present disclosure, a perfume dispersing device for dispersing a plurality of flavours of perfume is disclosed. The device comprises an input unit configured to receive an input from a user. The input indicates a selection of a flavour from a plurality of flavours of perfume. The device further comprises a compressor configured to generate pressure in an air tank of the perfume dispersing device. The air tank is filled with air. The device further comprises a processor configured to select a perfume holder from a plurality of perfume holders included in the perfume dispersing device based on the input from the user. Each perfume holder of the plurality of perfume holders contains a specific flavour of the plurality of flavours of perfume. The air tank is configured to release air pressure to the selected perfume holder. The perfume holder is configured to disperse the flavour indicated by the input from the user.

In some embodiments, the perfume dispersing device is connected to a mobile device through an audio jack.

In some embodiments, the compressor draws a current from the mobile device.

In some embodiments, the air pressure is released to the selected perfume holder through a network of pipes.

In some embodiments, each pipe of the network of pipes is connected to a corresponding perfume holder of the plurality of perfume holders.

In some embodiments, the user provides the input to the perfume dispersing device via a user interface displayed on a screen of the mobile device.

In some embodiments, the flavour indicated by the input from the user is dispersed in a form of mist.

In some embodiments, any of the above aspects may additionally have features identical with or corresponding to any of the various features as explained above for any of the other aspects.

BRIEF DESCRIPTION OF THE DRAWINGS

The foregoing will be apparent from the following more particular description of the example embodiments, as illustrated in the accompanying drawings in which reference characters refer to the same parts throughout the different views. The drawings are not necessarily to scale, emphasis instead being placed upon illustrating the example embodiments.

DETAILED DESCRIPTION

Figure 1:
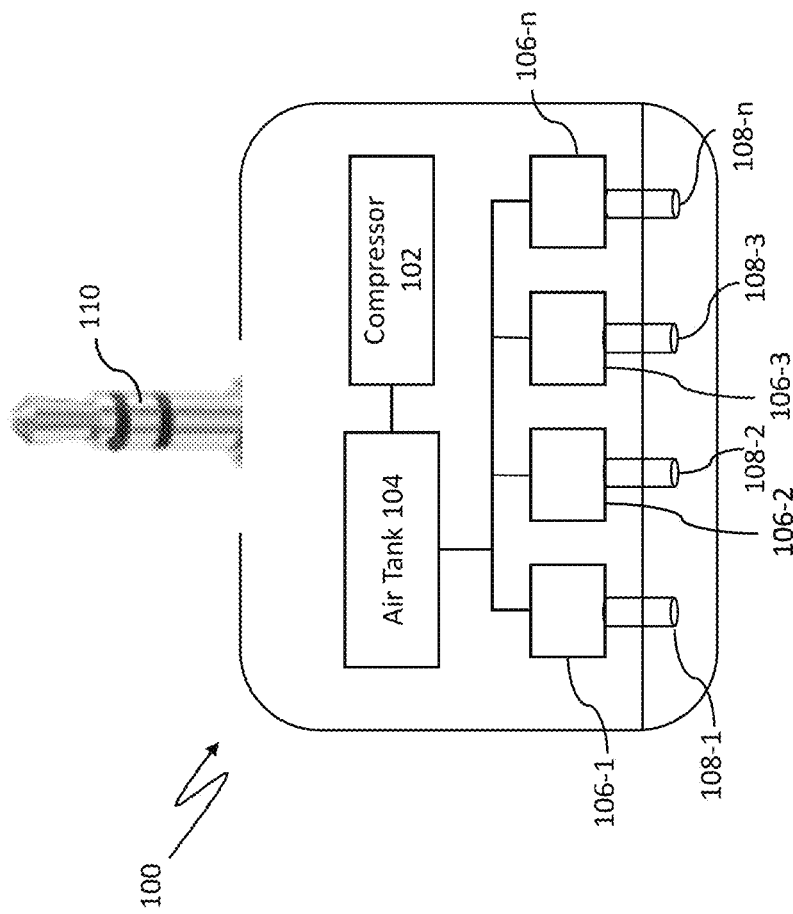
FIG. 1 illustrates a perfume dispersing device for dispersing a plurality of flavours of perfume, according to some embodiments of the present invention.

Aspects of the present disclosure will be described more fully hereinafter with reference to the accompanying drawings. The apparatus and methods disclosed herein can, however, be realized in many different forms and should not be construed as being limited to the aspects set forth herein. Like numbers in the drawings refer to like elements throughout.

Reference will now be made in detail to embodiments, examples of which are illustrated in the accompanying drawings. In the following detailed description, numerous specific details are set forth in order to provide a thorough understanding of the present invention. However, it will be apparent to one of ordinary skill in the art that the present invention may be practiced without these specific details. In other instances, well-known methods, procedures, components, circuits, and networks have not been described in detail so as not to unnecessarily obscure aspects of the embodiments.

The terminology used herein is for the purpose of describing particular aspects of the disclosure only and is not intended to limit the invention. It should be emphasized that the term "comprises/comprising" when used in this specification is taken to specify the presence of stated features, integers, steps, or components, but does not preclude the presence or addition of one or more other features, integers, steps, components, or groups thereof. As used herein, the singular forms "a", "an", and "the" are intended to include the plural forms as well, unless the context clearly indicates otherwise.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Embodiments of the present disclosure will be described and exemplified more fully hereinafter with reference to the accompanying drawings. The solutions disclosed herein can, however, be realized in many different forms and should not be construed as being limited to the embodiments set forth herein.

It will be appreciated that when the present disclosure is described in terms of a method, it may also be embodied in one or more processors and one or more memories coupled to the one or more processors, wherein the one or more memories store one or more programs that perform the steps, services, and functions disclosed herein when executed by the one or more processors.

FIG. 1 illustrates a perfume dispersing device 100 for dispersing a plurality of flavours of perfume, according to some embodiments of the present invention. The perfume dispersing device 100 may comprise a compressor 102 for generating pressure in an air tank 104 of the perfume dispersing device 100. The air tank 104 may be filled with air. The amount of air in the air tank 104 must be appropriate for dispersing each flavour of the perfume.

Further, the perfume dispersing device 100 may comprise a plurality of perfume holders 106-1 through 106-n. Each perfume holder of the plurality of perfume holders 106-1 through 106-n may comprise a sample of a flavour of the perfume. Each flavour is different from other flavours of the perfume. An amount of the sample of the flavour is appropriate for dispersing in the air. The plurality of perfume holders 106-1 through 106-n may be connected with the air tank 104 through a pipe network. The pipe network may comprise a plurality of pipes for releasing the air from the air tank 104 to the plurality of perfume holders 106-1 through 106-n.

Each perfume holder of the plurality of perfume holders 106-1 through 106-n may be connected with a plurality of nozzles 108-1 through 108-n. Each nozzle of the plurality of nozzles 108-1 through 108-n may be adapted to disperse a corresponding flavour of the perfume.

The perfume dispersing device 100 may comprise an audio jack 110 for connecting the perfume dispersing device 100 with a mobile device. Further, the perfume dispersing device 100 may draw current from the mobile device for operation of components of the perfume dispersing device 100. The mobile device may control selection of the perfume holder and may control the compressor 102 for providing air compression in the air tank 104.

Figure 2:
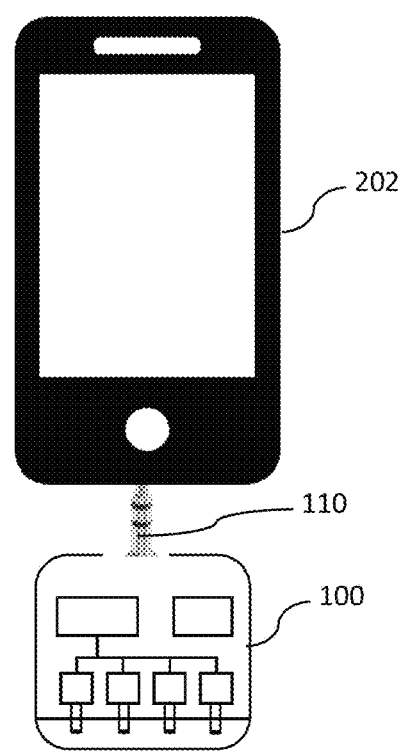
FIG. 2 illustrates connection of a perfume dispersing device with a mobile device, according to some embodiments of the present invention.

FIG. 2 illustrates connection of the perfume dispersing device 100 with a mobile device 202, according to some embodiments of the present invention. As illustrated in FIG. 2, the perfume dispersing device 100 may be connected to the mobile device 202 through the audio jack 110. The mobile device 202 may control the operation of the perfume dispersing device 100. The mobile device 202 may provide a user interface (UI) to a user for selection of a flavour of the perfume. The UI may be displayed on a screen of the mobile device 202. The screen may be a touch control screen for taking input from the user. The UI may contain a list of flavours available with the manufacturer. The manufacturer may provide the perfume dispersing device 100 to the user instead of providing the sample of each flavour of the perfume to the user.

In operation, the user may connect the perfume dispersing device 100 to the mobile device 202 through the audio jack 110. The mobile device 202 may display the UI on the screen of the mobile device 202. The user may select a flavour of the perfume on the UI. After selection of the flavour of the perfume, the mobile device 202 may instruct the perfume dispersing device 100 to select corresponding perfume holder from the plurality of perfume holders 106-1 through 106-n.

Further, the perfume dispersing device 100 may draw current from the mobile device 202 through the audio jack 110. The compressor 102 may utilize the current drawn from the mobile device 202 to generate pressure in the air tank 104. The air tank 104 may release air in the corresponding perfume holder of the selected flavour of the perfume. The released air may pass through the pipe network to reach the corresponding perfume holder. The perfume holder may comprise sample of the corresponding flavour of the perfume. The corresponding flavour may be dispersed from the perfume holder through the corresponding nozzle.

The flavour may be dispersed in the air. The user may smell the flavour and selected corresponding flavour of the perfume from the manufacturer.

Figure 3:
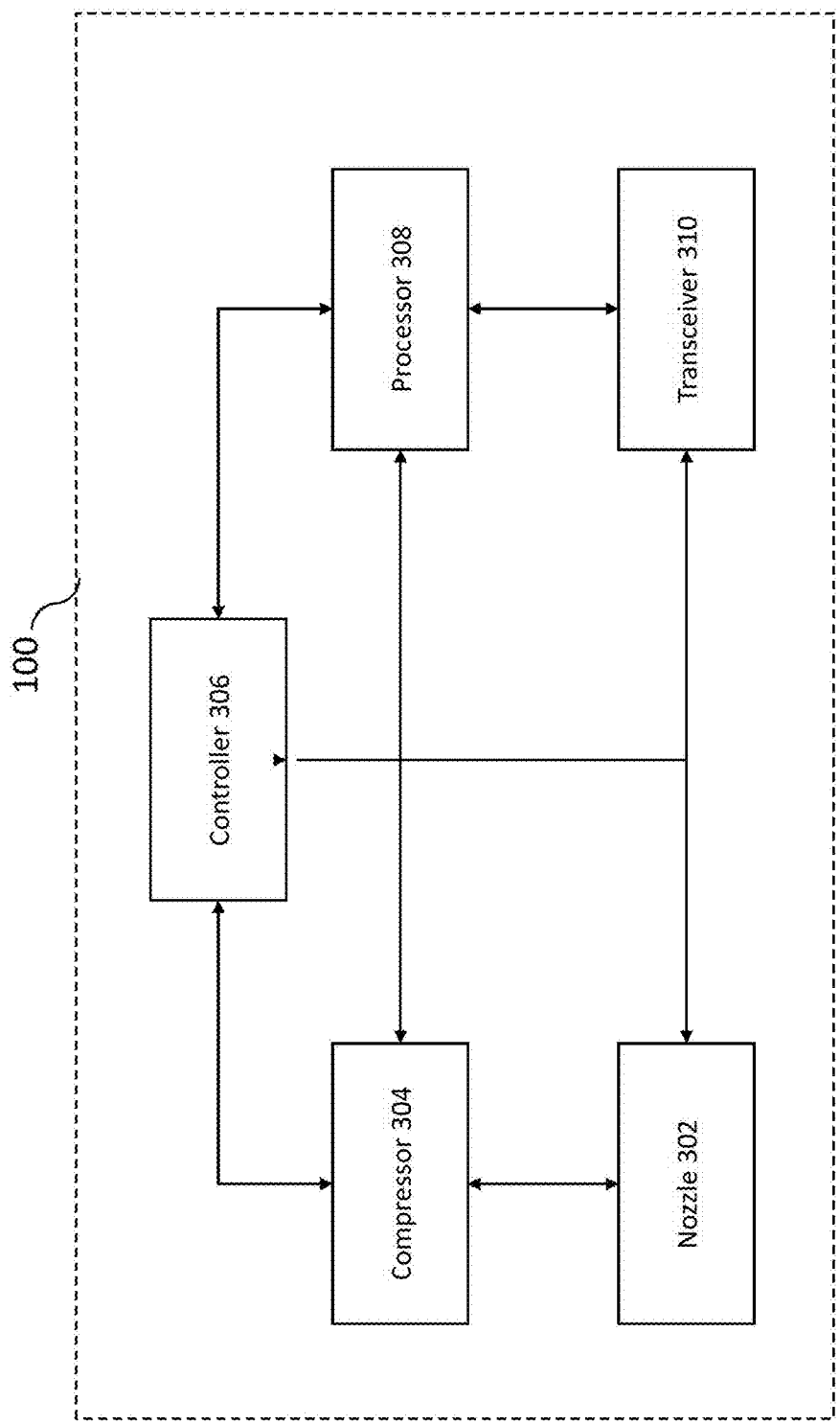
FIG. 3 illustrates a schematic block diagram illustrating an example apparatus, according to some embodiments of the present invention.

FIG. 3 illustrates a schematic block diagram illustrating an example apparatus, according to some embodiments of the present invention. The device 100 may be capable of dispersing a plurality of flavours of perfume.

According to at least some embodiments of the present invention, the apparatus 100 in FIG. 3 comprises one or more modules. These modules may e.g. be a nozzle 302, a compressor 304, a controller 306, a processor 308, and a transceiver 310. The controller 306, may in some embodiments be adapted to control the above mentioned modules.

The nozzle 302, the compressor 304, the processor 308, and the transceiver 310 as well as the controller 306, may be operatively connected to each other.

Optionally, the transceiver 310 may be adapted to receive an instruction for usage of the device 100.

The controller 306 may be adapted to control the steps as executed by the device 100 according to the instructions received by the transceiver 310. For example, the controller 306 may be adapted to activate the compressor 304 (as described above in conjunction with the FIG. 1).

Further, the processor 308 is adapted to perform the method and FIG. 1 in conjunction with the controller 306.

The nozzle 302 is adapted disperse the flavour of the perfume in the air.

Figure 4:
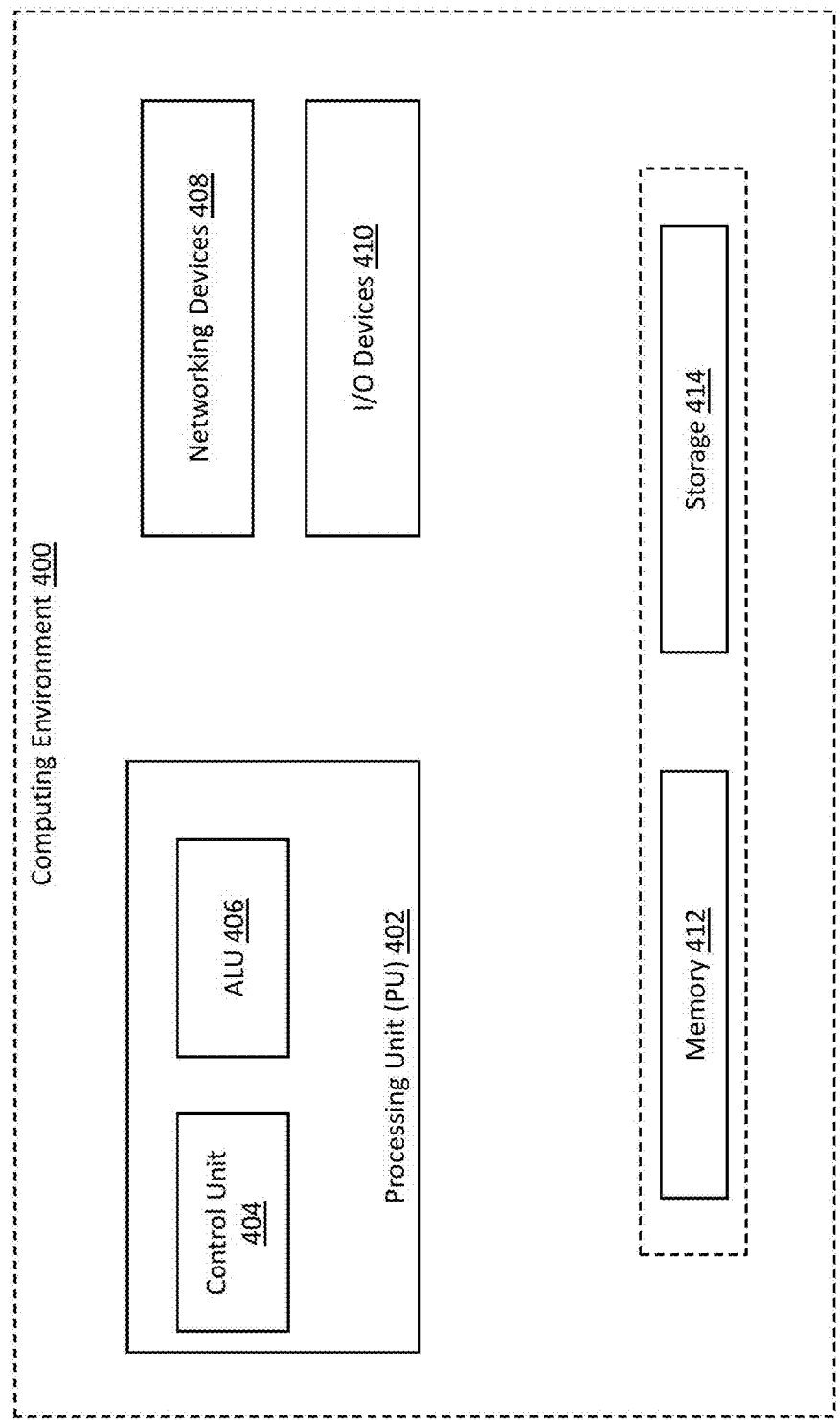
FIG. 4 illustrates an example computing environment implementing a perfume dispersing device, according to some embodiment of the present invention.

FIG. 4 illustrates an example computing environment implementing a device for dispersing a plurality of flavours of perfume, according to some embodiment of the present invention. As depicted in FIG. 4, the computing environment 400 comprises at least one processing unit 402 that is equipped with a control unit 404 and an Arithmetic Logic Unit (ALU) 406, a plurality of networking devices 408 and a plurality Input output, I/O devices 410, a memory 412, and a storage 414. The processing unit 402 may be responsible for implementing the method described in FIGS. 1-2. For example, the processing unit 402 may in some embodiments be equivalent to the processor of the mobile device and the UE described above in conjunction with the FIGS. 1-2. The processing unit 402 is capable of executing software instructions stored in memory 412. The processing unit 402 receives commands from the control unit 404 in order to perform its processing. Further, any logical and arithmetic operations involved in the execution of the instructions are computed with the help of the ALU 406.

The computer program is loadable into the processing unit 402, which may, for example, be comprised in an electronic apparatus. When loaded into the processing unit 402, the computer program may be stored in the memory 412 associated with or comprised in the processing unit 402. According to some embodiments, the computer program may, when loaded into and run by the processing unit 402, cause execution of method steps according to, for example, any of the methods illustrated in FIGS. 1-2 or otherwise described herein.

The overall computing environment 400 may be composed of multiple homogeneous and/or heterogeneous cores, multiple CPUs of different kinds, special media and other accelerators. Further, the plurality of processing unit 402 may be located on a single chip or over multiple chips.

The algorithm comprising of instructions and codes required for the implementation are stored in either the memory 412 or the storage 414 or both. At the time of execution, the instructions may be fetched from the corresponding memory 412 and/or storage 414, and executed by the processing unit 402.

In case of any hardware implementations various networking devices 408 or external I/O devices 410 may be connected to the computing environment to support the implementation through the networking devices 408 and the I/O devices 410.

The embodiments disclosed herein can be implemented through at least one software program running on at least one hardware device and performing network management functions to control the elements. The elements shown in FIG. 4 include blocks which can be at least one of a hardware device, or a combination of hardware device and software module.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the scope of the disclosure.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the scope of the disclosure.

The systems and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user's computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer-readable media such as RAMs, ROMs, flash memory, EEPROMs, optical devices (CD or DVD), hard drives, and floppy drives, or any suitable device. The computer-executable component can be a processor but any suitable dedicated hardware device can (alternatively or additionally) execute the instructions.

As a person skilled in the art will recognize from the previous detailed description and the figures and claims, modifications and changes can be made to the embodiments of the invention without departing from the spirit and scope of this invention as defined in the following claims.

The invention claimed is:

1. A method for dispersing a plurality of flavours of perfume, the method being performed by a perfume dispersing device, the method comprising:
   receiving, from a user, an input indicating a selection of a flavour from a plurality of flavours of perfume;
   generating, from a compressor of the perfume dispersing device, pressure in an air tank of the perfume dispersing device, wherein the air tank is filled with air;
   selecting, by a processor of the perfume dispersing device, a perfume holder from a plurality of perfume holders included in the perfume dispersing device based on the input from the user, wherein each perfume holder of the plurality of perfume holders contains a specific flavour of the plurality of flavours of perfume;
   releasing, by the air tank, air pressure to the selected perfume holder; and
   dispersing, by the selected perfume holder, the flavour indicated by the input from the user,
   wherein the perfume dispersing device is connected to a mobile device through an audio jack.

2. The method as claimed in claim 1, wherein the compressor draws a current from the mobile device.

3. The method as claimed in claim 1, wherein the air pressure is released to the selected perfume holder through a network of pipes.

4. The method as claimed in claim 3, wherein each pipe of the network of pipes is connected to a corresponding perfume holder of the plurality of perfume holders.

5. The method as claimed in claim 1, wherein the user provides the input to the perfume dispersing device via a user interface displayed on a screen of the mobile device.

6. The method as claimed in claim 1, wherein the flavour indicated by the input from the user is dispersed in a form of mist.

7. The method as claimed in claim 1, wherein each perfume holder of the plurality of perfume holders is connected through a nozzle to dispersing the flavour of perfume.

8. A perfume dispersing device for dispersing a plurality of flavours of perfume, the device comprising:
   an input unit configured to receive an input from a user, wherein the input indicates a selection of a flavour from a plurality of flavours of perfume;
   a compressor configured to generate pressure in an air tank of the perfume dispersing device, wherein the air tank is filled with air;
   a processor configured to select a perfume holder from a plurality of perfume holders included in the perfume dispersing device based on the input from the user, wherein each perfume holder of the plurality of perfume holders contains a specific flavour of the plurality of flavours of perfume;
   the air tank is configured to release air pressure to the selected perfume holder; and
   the perfume holder is configured to disperse the flavour indicated by the input from the user,
   wherein the perfume dispersing device is connected to a mobile device through an audio jack.

9. The device as claimed in claim 8, wherein the compressor draws a current from the mobile device.

10. The device as claimed in claim 8, wherein the air pressure is released to the selected perfume holder through a network of pipes.

11. The device as claimed in claim 10, wherein each pipe of the network of pipes is connected to a corresponding perfume holder of the plurality of perfume holders.

12. The device as claimed in claim 8, wherein the user provides the input to the perfume dispersing device via a user interface displayed on a screen of the mobile device.

13. The device as claimed in claim 8, wherein the flavour indicated by the input from the user is dispersed in a form of mist.

14. The device as claimed in claim 8, wherein each perfume holder of the plurality of perfume holders is connected through a nozzle to dispersing the flavour of perfume.

* * * * *